United States Patent
Godart et al.

(10) Patent No.: US 10,100,345 B2
(45) Date of Patent: *Oct. 16, 2018

(54) METHOD FOR THE PRODUCTION OF DOCOSAHEXAENOIC ACID (DHA) AND/OR OF CAROTENOIDS FROM AURANTIOCHYTRIUM

(71) Applicant: FERMENTALG, Libourne (FR)

(72) Inventors: Francois Godart, Vayres (FR); Julien Pagliardini, Bordeaux (FR); Cyril Rols, Marseilles (FR); Pierre Calleja, Libourne (FR)

(73) Assignee: FERMENTALG, Libourne (FR)

( * ) Notice: Subject to any disclaimer, the term of this patent is extended or adjusted under 35 U.S.C. 154(b) by 72 days.

This patent is subject to a terminal disclaimer.

(21) Appl. No.: 14/904,369

(22) PCT Filed: Jul. 15, 2014

(86) PCT No.: PCT/FR2014/051808
§ 371 (c)(1),
(2) Date: Jan. 11, 2016

(87) PCT Pub. No.: WO2015/004402
PCT Pub. Date: Jan. 15, 2015

(65) Prior Publication Data
US 2016/0153021 A1  Jun. 2, 2016

(30) Foreign Application Priority Data
Jul. 12, 2013  (FR) ...................................... 13 56917

(51) Int. Cl.
| | |
|---|---|
| *C12N 1/12* | (2006.01) |
| *C12P 23/00* | (2006.01) |
| *C12R 1/89* | (2006.01) |
| *C12N 13/00* | (2006.01) |
| *C12P 7/64* | (2006.01) |

(52) U.S. Cl.
CPC ................ *C12P 23/00* (2013.01); *C12N 1/12* (2013.01); *C12N 13/00* (2013.01); *C12P 7/6427* (2013.01); *C12P 7/6472* (2013.01); *C12R 1/89* (2013.01)

(58) Field of Classification Search
None
See application file for complete search history.

(56) References Cited

U.S. PATENT DOCUMENTS

| | | |
|---|---|---|
| 2009/0209014 A1 | 8/2009 | Chi et al. |
| 2013/0171702 A1 | 7/2013 | Calleja |
| 2015/0037838 A1 | 2/2015 | Romari et al. |

FOREIGN PATENT DOCUMENTS

| | | |
|---|---|---|
| EP | 2559342 | 2/2013 |
| WO | 2012-035262 | 3/2012 |
| WO | 2013-136028 | 9/2013 |

OTHER PUBLICATIONS

Park et al. Biotechnol. Bioprocess Eng. 2000, vol. 5, No. 3, pp. 186-190.*
Bligh et al., "A Rapid Method of Total Lipid Extraction and Purification," Canadian Journal of Biochemistry and Physiology, vol. 37, No. 8, Aug. 1959, pp. 911-917.
Chatdumrong et al., "Optimization of Docosahexaenoic Acid (DHA) Production and Improvement of Astaxanthin content in a Mutant Schizochytrium limacinum Isolated from Mangrove forest in Thailand," Kasetsart Journal, vol. 41, Jan. 1, 2007, pp. 324-334.
Hong et al., "Production of Lipids containing high levels of Docosahexaenoic Acid by a newly isolated Microalga, *Aurantiochytrium* sp. KRS101," Applied Biochemistry and Biotechnology, vol. 164, No. 8, Mar. 22, 2011, pp. 1468-1480.
Jakobsen et al., "Accumulation of Docosahexaenoic Acid-rich lipid in thraustochytrid *Aurantiochytrium* sp. strain T66: affects of N and P starvation and O2 limitation," Applied Microbiology and Biotechnology, vol. 80, No. 2, Jun. 17, 2008, pp. 297-306.
Wright et al., "Improved HPLC method for the analysis of chlorophylls and carotenoids from marine phytoplankton," Marine Ecology Progress Series, vol. 77, Nov. 1991, pp. 183-196.
Yokoyama et al., "Taxonomic rearrangement of the genus Schizochytrium sensu lato based on morphology, chemotaxonomic characteristics, and 18S rRNA gene phylogeny (Thraustochytriaceae, Labryinthulomycetes): emendation for Schizochytrium and erection of Aurantiochytrium and Oblongichytrium gen. nov.," Mycoscience, vol. 18, No. 4, Aug. 6, 2007, pp. 199-211.

* cited by examiner

*Primary Examiner* — Irene Marx
(74) *Attorney, Agent, or Firm* — Young & Thompson (57) ABSTRACT

Disclosed are novel strains of protists belonging to the *Aurantiochytrium* genus that allow the high yield production of lipids and carotenoids, in particular docosahexaenoic acid (DHA) and canthaxanthin and/or astaxanthin, in mixotrophic mode, in particular, using variable and/or discontinuous provision of light, in particular in the form of flashes.

6 Claims, 3 Drawing Sheets

METHOD FOR THE PRODUCTION OF DOCOSAHEXAENOIC ACID (DHA) AND/OR OF CAROTENOIDS FROM AURANTIOCHYTRIUM

The invention relates to a method of culture in mixotrophic mode, in particular in the presence of discontinuous and/or variable illumination with light, of a protist of the Labyrinthulomycetes class, in particular of the genus *Aurantiochytrium*. The method gives a high yield of biomass and enrichment of the thus cultured protists in lipids and carotenoids and more particularly in docosahexaenoic acid (DHA) and canthaxanthin and/or astaxanthin. The method thus makes it possible to culture strains of the genus *Aurantiochytrium* with mixotrophic character, and having a high yield of lipids and/or carotenoids, and more particularly of polyunsaturated fatty acids and of canthaxanthin and/or astaxanthin. The invention also relates to novel strains of protist belonging to the genus *Aurantiochytrium*, particularly adapted to the production of lipids and of carotenoids. These novel strains of the genus *Aurantiochytrium* are useful for producing docosahexaenoic acid (DHA) and canthaxanthin and/or astaxanthin in mixotrophic mode.

Preamble

Among the polyunsaturated fatty acids, certain highly unsaturated fatty acids (HUFA) of the omega-3 series (PUFA-$\omega$3), in particular eicosapentaenoic acid (EPA or C20:5 $\omega$3) and docosahexaenoic acid (DHA or C22:6 $\omega$3), and of the omega-6 series (PUFA-$\omega$6), in particular arachidonic acid (ARA or AA or eicosatetraenoic acid C20:4 $\omega$6) have a recognized nutritional importance, and have strong potential in terms of therapeutic applications.

Regarded as an essential nutrient, DHA is necessary to the normal functional development of cells, and plays a crucial role in various biochemical processes and functions. Its polyunsaturated nature confers on it a crucial importance in relation to the properties of the cell membrane, both in plants and in animals: fluidity, flexibility and selective permeability allowing for example effective adaptation, and even survival, at low temperatures, in particular in fish.

DHA is a major structural constituent of the human brain and it is its principal fatty acid. DHA represents 15-20% of the cerebral cortex (an adult's brain contains at least 20 g of DHA) and 30-60% of the retina. It is essential for the development of the central nervous system and for retinal function, by incorporation into the cell membranes, and plays a major role in the acquisition and satisfactory maintenance of the mechanisms of vision and memory.

Fish oils, from the fishing industry, are currently the main commercial source of this type of fatty acids. However, while these oils find new applications (food supplement in aquaculture, incorporation in margarines), marine halieutic resources are becoming scarce because of intensive fishing activity.

Therefore, new sources of these fatty acids such as EPA, DHA and ARA have to be sought in order to meet, in the future, the increasing market demand for this type of polyunsaturated fatty acids.

The protists are microorganisms with a simple cellular organization, i.e. they are generally unicellular and sometimes multicellular but without specialized tissues. They may be autotrophic or heterotrophic.

The protists are currently the subject of numerous industrial projects since some species are capable of accumulating or secreting significant quantities of lipids, in particular polyunsaturated fatty acids.

In addition to their capability of synthesizing fatty acids de novo, protists provide several advantages compared to fish oils: they may be cultured in vitro under controlled conditions, which allows production of a biomass of a relatively constant biochemical composition, and, in addition, unlike fish oils, their lipids contain little or no cholesterol.

Finally, the lipids produced by protists have a simpler fatty acid profile than that of fish oils, which limits the steps for separating the fatty acids of interest.

Furthermore, carotenoids are also molecules of interest. They are generally used as pigments, but they also have a significant role for human health as antioxidant agents. Finally, they have the ability to stimulate the immune system.

The Thraustochytrides, in particular *Aurantiochytrium*, are known to produce DHA when they are cultured in heterotrophic mode [W. K. Hong et al. (2011); Production of lipids containing high levels of docosahexaenoic acid by a newly isolated microalga, *Aurantiochytrium* sp. KRS101. Appl. Biochem. Biotechnol.: 164(8):1468-80]. *Aurantiochytrium* is also known to produce carotenoids, such as astaxanthin, zeaxanthin, canthaxanthin, echinenone, beta-carotene and phoenicoxanthin [Yokoyama, R, Honda, D. (2007) Taxonomic rearrangement of the genus *Schizochytrium* sensu lato based on morphology, chemotaxonomic characteristics, and 18S rRNA gene phylogeny (Thraustochytriaceae, Labyrinthulomycetes): emendation for *Schizochytrium* and erection of *Aurantiochytrium* and *Oblongichytrium* gen. nov.; *Mycoscience*, Vol. 48, pp 199-211].

For implementing the production of fatty acids and carotenoids by protists on an industrial scale, several factors must be taken into account. For example, cultures may be carried out under autotrophic, mixotrophic or heterotrophic conditions depending on the strain, the temperature, the lighting conditions and the size of the fermenters. For example, cultures may also be carried out in 1 L containers, in a laboratory, in photo-bioreactors, and in 100,000 L containers or in open ponds (several hectares). However, the costs of energy and other resources such as manpower and the ease of monitoring the culture must be taken into account for developing ideal culture conditions.

In any case, it would be desirable to be able to obtain greater yields of DHA and carotenoids than that described in the prior art for more efficient and more cost-effective industrial exploitation.

Thus, it is preferable to have a yield that is as high as possible (for example above 80 g/l of dry matter, more than 30% of fatty acids by weight relative to the total weight of dry matter, and more than 0.1% by weight of carotenoids to the total weight of dry matter).

The effect of light on growth is not restricted to photosynthetic organisms (plants, cyanobacteria, microalgae and macroalgae). Certain non-chlorophyl organisms have photoreceptors that enable them to capture the light energy that is essential for their development. Photoreceptors such as phytochrome represent a typical example of a light sensor that controls the development of the organism that possesses it. To date, different photoreceptors have been described, namely, among others, the accessory pigments, the cryptochromes and phototropins.

In addition, regarding the modes of cultures three types of fermentation processes exist which are commonly used in the field of biomass production.

the discontinuous (or "batch") mode:

The tank is filled with the sterilized culture medium, then the inoculum. The fermentation then takes place without the supplementary major addition of medium (mainly the pH correctives and anti-foaming agents). The volume remains constant and the productivity of biomass is relatively low. At the end of fermentation, the fermenter is emptied and its content is replaced.

the semi-continuous (or "fed-batch") mode:

This production method is based on the progressive feeding with nutritive substrate during the culture. This mode is generally used to achieve a high cell density in the fermenter.

the continuous mode:

In this method, a fermenter is used which is commonly called a "chemostat" into which a fresh culture medium is continuously added, while the culture liquid is continuously drawn-off in order to keep the culture volume constant.

The growth rate of the cells can be monitored by modifying the rate of feeding with nutritive matter while respecting the physiological limits of each type of cell or strain (depending on its specific maximum growth rate ($\mu$max) under the specific process conditions).

The continuous mode allows the culture of the microorganisms in a given state of physiological equilibrium corresponding to an equilibrium between the growth of the biomass and the production of metabolite(s) of interest.

In the state of equilibrium, the cells grow at a constant rate and all the parameters of the culture remain constant (pH, volume, dissolved oxygen concentration, concentrations of nutritive elements and products, cell density, etc.).

The continuous mode has, in particular, the following advantages:
- the overall production cost of biomass is reduced (less cleaning, sterilization and culture operations, immobilization of equipment at fermentation level);
- the productivity (quantity of biomass produced per hour) is increased;
- the continuous recovery of the biomass makes it possible to facilitate operations downstream by optimizing the dimensioning of the equipment.

However, the continuous processes also have drawbacks, in particular when the production of the molecule of interest is dissociated or partially dissociated from the cell growth phase. Thus, when a substance of interest is produced outside this optimum growth phase (for example at the end of culture, during the stationary phase of the culture), it is more difficult to obtain performances that are compatible with economic interests.

Other constraints linked with the continuous mode are:
- management of the effluents in greater quantity (lower concentration of biomass),
- loss of unconsumed raw materials (residual substrates) can also have an impact on the processes downstream (extraction, drying etc.).

It is, therefore desirable to produce cultures of the strains of *Aurantiochytrium* for the production of DHA and/or of canthaxanthin and/or of astaxanthin according to the culture mode which will make it possible to achieve a level of biomass and of the molecules of interest which is cost-effective on an industrial scale.

In order to improve the yield of DHA and of carotenoids, in particular of canthaxanthin and/or of astaxanthin, the culture method according to the invention is carried out in mixotrophic mode, i.e. with a light supply, preferably, with a variable and/or discontinuous intensity and in the presence of a supply of organic substrate.

It is to be understood that the term mixotrophic is usually employed with regard to strains having a chloroplast, able to develop in the presence of light, using two sources of carbon (organic and inorganic). In the case of the strains of the genus *Aurantiochytrium*, such a chloroplast has not been identified. However, as the strain is both heterotrophic and reactive to light, the term mixotrophic will be extended in the sense of the invention to this category of strain. The term "photo-heterotroph" can also be used to indicate such a strain.

Thus, it was after numerous screening experiments on strains that the applicant succeeded in isolating protist strains of the genus *Aurantiochytrium*, that can be cultured in mixotrophic mode, and allowing, under the conditions of the present invention, a high-yield production of polyunsaturated fatty acids and carotenoids, notably DHA and carotenoids, in particular canthaxanthin and astaxanthin.

Strains representative of the novel strains of *Aurantiochytrium* thus isolated and selected, were deposited at the CCAP (Culture Collection of Algae and Protozoa, Scottish Association for Marine Science, Dunstaffnage Marine Laboratory, Oban, Argyll PA37 1QA, Scotland, United Kingdom).

Thus the strain (FCC 1324) was deposited with the CCAP on Jun. 21, 2013 according to the provisions of the Treaty of Budapest, under the accession number CCAP 4062/1.

The strains FCC 31 (accession number CCAP 4062/2); FCC 1311 (accession number CCAP 4062/3); FCC 1319 (accession number CCAP 4062/4); FCC 1325 (accession number CCAP 4062/5) and FCC 1479 (accession number CCAP 4062/6), were deposited with the CCAP on Jul. 8, 2014 according to the provisions of the Treaty of Budapest.

According to an embodiment, the culture in mixotrophic mode is carried out under illumination conditions that are discontinuous and/or variable over time, the illumination having variations in intensity, the amplitude of which is comprised between 5 $\mu mol \cdot m^{-2} \cdot s^{-1}$ and 1,000 $\mu mol \cdot m^{-2} \cdot s^{-1}$, these variations taking place between 2 and 3,600 times per hour. The amplitude of the variations in intensity is comprised between 70 and 300 $\mu mol \cdot m^{-2} \cdot s^{-1}$ and, preferably, between 100 and 200 $\mu mol \cdot m^{-2} \cdot s^{-1}$.

DETAILED DESCRIPTION

The present invention therefore relates to a method of culture of protists of the Labyrinthulomycetes class, in particular of the Thraustochytrid family, in particular of the genus *Aurantiochytrium*, in mixotrophic mode, in particular under conditions of illumination that are discontinuous and/or variable over time.

The invention also relates to a method for the production of DHA and/or of carotenoid(s), in particular of canthaxanthin and/or of astaxanthin, comprising the following step:

a) culture in mixotrophic mode of one or more strains of the genus *Aurantiochytrium*.

The illumination preferentially has variations in intensity, the amplitude of which is generally comprised between 5 $\mu mol \cdot m^{-2} \cdot s^{-1}$ and 1,000 $\mu mol \cdot m^{-2} \cdot s^{-1}$, preferably between 30 and 400 $\mu mol \cdot m^{-2} \cdot s^{-1}$. According to an embodiment of the invention these variations may generally take place between 2 and 3,600 times per hour, preferably between 2 and 200 times per hour. This light supply may comprise phases of discontinuous and/or variable illumination, with variations in intensity that may have identical or different amplitudes.

According to an embodiment the light supply is carried out in the form of flashes. According to an embodiment a flash has a duration comprised between 1/10 second and 10 minutes, preferably 5 seconds and 10 minutes, more preferably between 10 seconds and 2 minutes, more preferentially between 20 seconds and 1 minute.

According to an embodiment, the number of flashes is between 5 and 3600, preferably between 10 and 150, preferentially between 15 and 100, and more preferentially between 20 and 50 times per hour.

According to an embodiment, the illumination of the cultures is ensured by an illumination device internal to the fermenter, preferably situated on the baffles inside the fermenter. According to a preferred embodiment the illumination sources are light emitting diodes.

According to an embodiment of the invention, the culture method in mixotrophic mode is carried out in the presence of from 100 mM to 1.5 M, preferably from 200 mM to 1.2 M, more preferentially from 250 mM to 1 M, and even more preferentially from 300 mM to 600 mM of an organic carbon-containing substrate. The substrate is supplied continuously during culture, in order to allow the cells to accumulate a high concentration of lipids and carotenoids. Additional substrate is added to the culture medium during the culture method in order to maintain a sufficient concentration.

Figure 1:
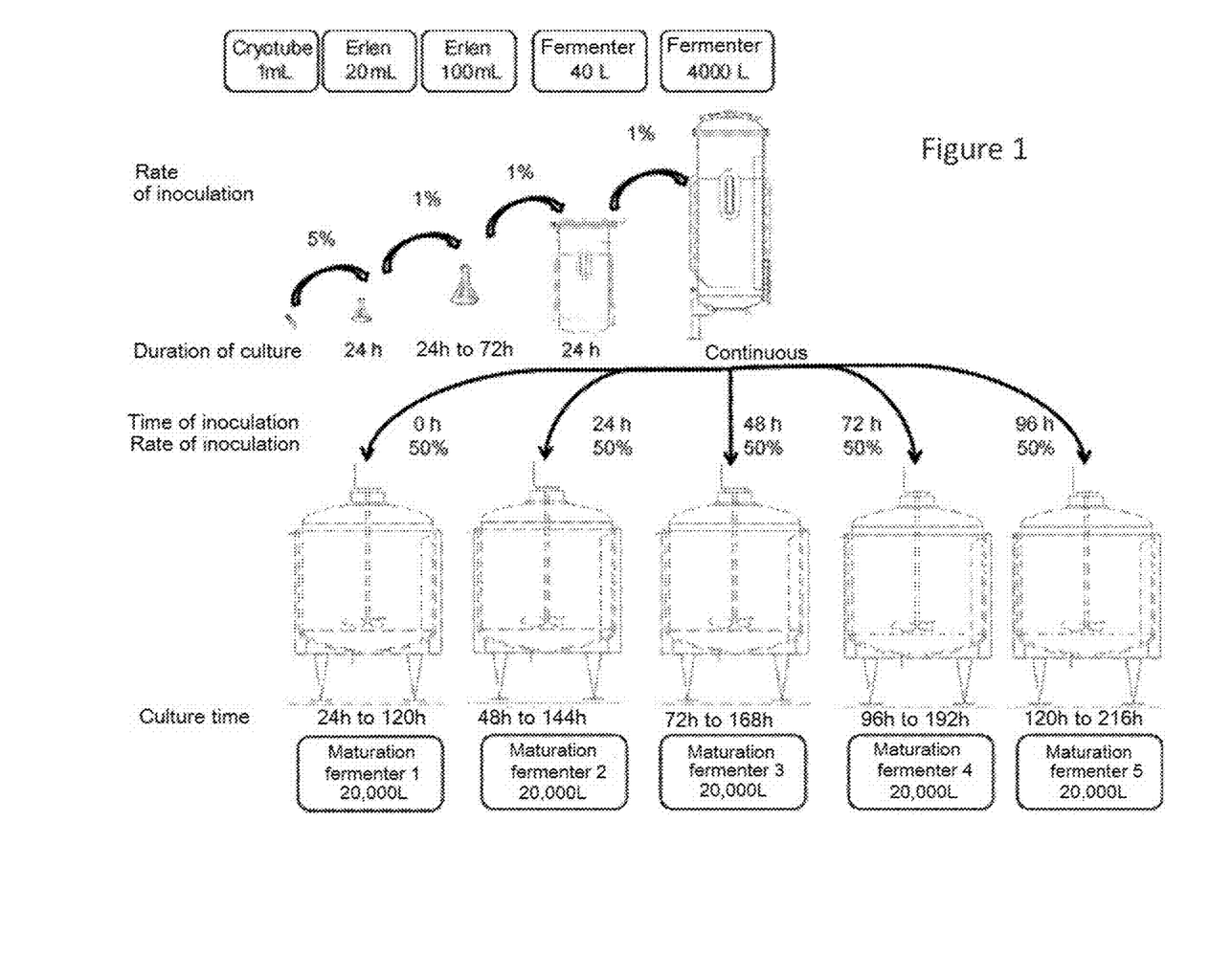
FIG. 1. Diagram of a method according to an embodiment of the invention, the "uncoupled method".

According to another embodiment of the invention, the culture method comprises the culture of cells in continuous mode under mixotrophic or heterotrophic conditions in a fermenter ("growth" step), then continuous feeding into fermenters operating in semi-continuous mode with the cells produced and their culture under mixotrophic conditions in said fermenters ("maturation" step) (see FIG. 1).

The method according to the invention has the advantage of increasing the yield of biomass obtained from the culture. It also has the advantage of enriching the thus cultured protists with polyunsaturated fatty acids, more particularly docosahexaenoic acid (DHA), and with carotenoids. The carotenoids which can be produced by *Aurantiochytrium* according to an embodiment of the invention are astaxanthin, zeaxanthin, canthaxanthin, echinenone, beta-carotene and phoenicoxanthin. According to an embodiment of the invention, the dominant carotenoids are canthaxanthin and astaxanthin.

Culture of this protist in mixotrophic mode is preferably carried out in the presence of 100 mM to 1.5 M, preferably from 200 mM to 1.2 M, more preferentially from 250 mM to 1 M, and even more preferentially from 300 mM to 600 mM of an organic carbon-containing substrate. The substrate is supplied continually during the culture, so as to allow the cells to accumulate a high concentration of lipids and carotenoids. Additional substrate is added to the culture medium during the culture method so as to maintain a constant concentration. This organic carbon-containing substrate comprises preferentially, in pure form or as a mixture: glucose, cellulose derivatives, saccharose and/or glycerol.

The organic carbon-containing substrate contained in the culture medium may consist of complex molecules or a mixture of substrates. The products resulting from the biotransformation of starch, for example starting from maize, wheat or potato, notably starch hydrolysates, which consist of small sized molecules, for example, form organic carbon-containing substrates suitable for mixotrophic culture of the protists according to the invention.

According to an embodiment, said organic carbon substrate present in the culture medium comprises at least 300 mM of glucose and/or glycerol.

This method is more particularly intended for the use of novel strains of the Labyrinthulomycetes class, in particular of the genus *Aurantiochytrium* (Kingdom: Chromista, Order: Thraustochytriales, Family: Thraustochytriaceae) [ITIS Catalogue of Life, 2010] selected for their mixotrophic character, and having a high yield of polyunsaturated fatty acids, notably DHA, and of carotenoids, notably canthaxanthin and/or astaxanthin, and in particular for their capability to be cultured with a supply of light greater than 10 $\mu$E, in a medium rich in organic elements, for example modified Verduyn medium (sea salts 15 g/L, $(NH_4)_2SO_4$ 3 g/L, $KH_2PO_4$ 1 g/L, $MgSO_4.7H_2O$ 0.5 g/L, $Na_2EDTA$ 24 mg/L, $ZnSO_4.7H_2O$ 3 mg/L, $MnCl_2.2H_2O$ 3 mg/L, $Na_2MoO_4.2H_2O$ 0.04 mg/L, $FeSO_4.7H_2O$ 10 mg/L, pantothenate 3.2 mg/L, thiamine hydrochloride 9.5 mg/L, vitamin B12 0.15 mg/L, antifoaming agent 0.1 mL/L), to which an organic carbon-containing substrate is added. Preferably, the organic carbon-containing substrate comprises glucose, glycerol, at a concentration equivalent to or greater than 300 mM.

By "strain", it is meant not only the natural strains of the genus *Aurantiochytrium*, but also the mutants of said natural strains.

By "mutants", it is meant an organism derived from the original strain, the gene pool of which has been modified either by a natural method, or by physico-chemical methods known to one skilled in the art being able to generate random mutations (UV etc.,), or by genetic engineering methods.

By "mixotrophic conditions", it is meant a culture with a light supply and a supply of organic carbon substrate.

By "heterotrophic conditions", it is meant a supply of organic carbon-containing substrate and in darkness.

Representative strains of the strains (of the genus *Aurantiochytrium*) according to the invention are the strains:

FCC 1324 isolated by the applicant and deposited at the CCAP under the number CCAP 4062/1;

FCC 31 isolated by the applicant and deposited at the CCAP under the number CCAP 4062/2;

FCC 1311 isolated by the applicant and deposited at the CCAP under the number CCAP CCAP 4062/3;

FCC 1319 isolated by the applicant and deposited at the CCAP under the number CCAP 4062/4;

FCC 1325 isolated by the applicant and deposited at the CCAP under the number CCAP 4062/5); and FCC 1479 isolated by the applicant and deposited at the CCAP under the number CCAP 4062/6.

These strains are capable of producing significant quantities of biomass as well as lipids and carotenoids, and more particularly of DHA and canthaxanthin and/or astaxanthin when they are cultured in mixotrophic mode in particular with a variable or discontinuous supply of light, according to a preferred embodiment of the invention.

According to the ongoing taxonomic analyses, the strains FCC 1324 (CCAP 4062/1), FCC 31 (CCAP 4062/2), FCC 1311 (CCAP 4062/3), FCC 1319 (CCAP 4062/4), FCC 1325 (CCAP 4062/5) and FCC 1479 (CCAP 4062/6) belong to the genus *Aurantiochytrium*.

The invention relates to these novel strains FCC 1324 (CCAP 4062/1), FCC 31 (CCAP 4062/2), FCC 1311 (CCAP 4062/1), FCC 1319 (CCAP 4062/4), FCC 1325 (CCAP 4062/5) and FCC 1479 (CCAP 4062/6).

Certain strains belonging to the species *Aurantiochytrium mangrovei* differ from each other. The following strains have similar characteristics: CCAP 4062/1, CCAP 4062/2, CCAP 4062/3, CCAP 4062/4, CCAP 4062/5, CCAP 4062/6. For example, the strains CCAP 4062/1 and a strain of the prior art of *Aurantiochytrium mangrovei* FCC 1104 (deposit number CCAP 4087/1) differ in their morphological characteristics and their growth profiles.

Figure 2:
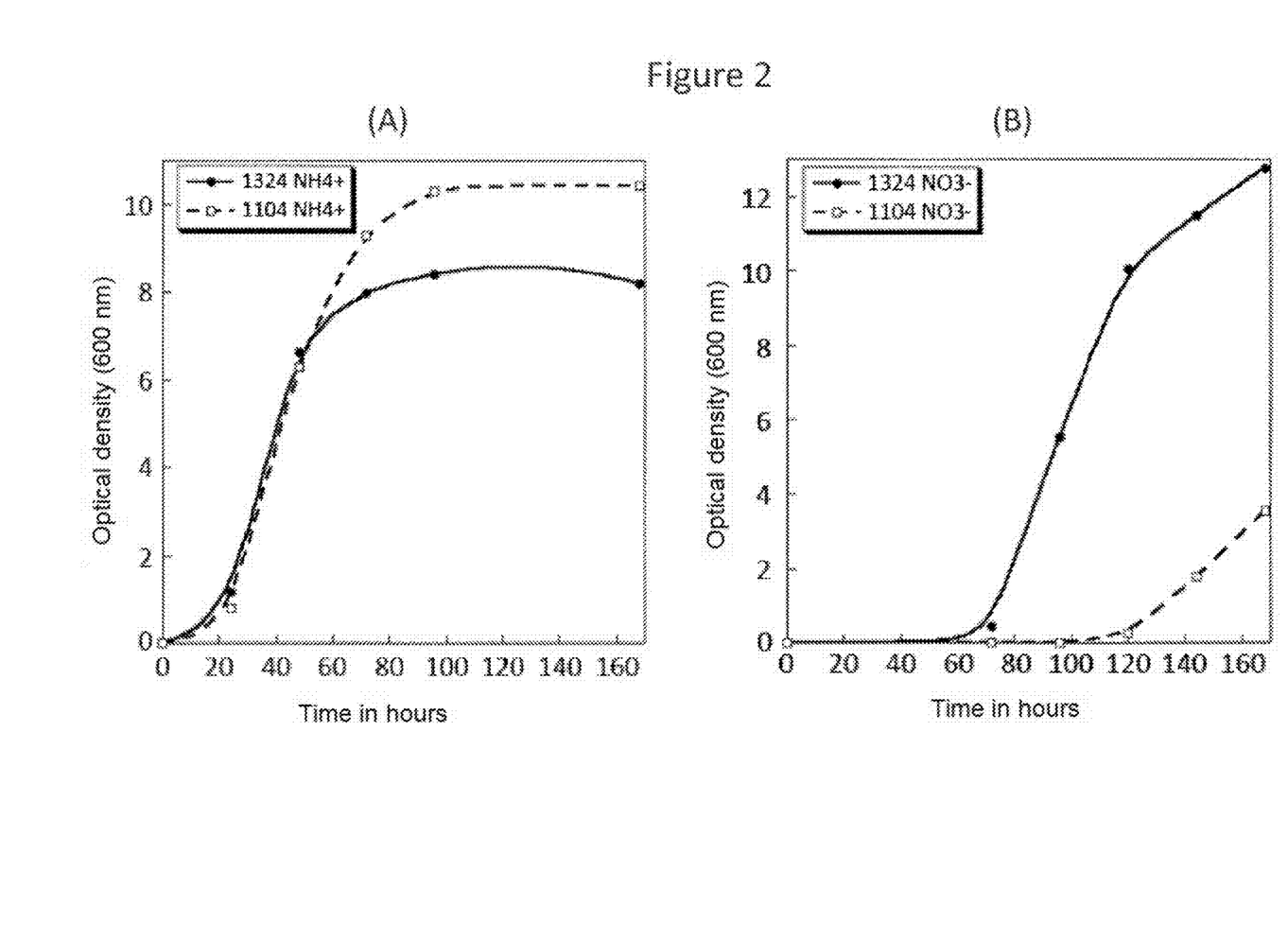
FIG. 2. Comparison of growth between the strain FCC 1324 (CCAP 4062/1) and the strain FCC 1104 of *Aurantiochytrium mangrovei* (deposit number CCAP4087/1). (A) Growth in the presence of $NH_4^+$ as nitrogen source. (B) Growth in the presence of $NO_3^-$ as nitrogen source.

The inventors were able to see the distinction by means of growth tests and morphological analyses. Under the same culture conditions, the growth of these two strains is different, both in terms of the rate of growth and in terms of the optical density attained during the saturation phase (see FIGS. 2A and 2B). Effectively, the strain CCAP 4087/1 develops more on a medium containing $NH_4^+$ than the strain CCAP 4062/1, while the reverse is observed using a medium containing $NO_3^-$ as nitrogen source.

Figure 3:
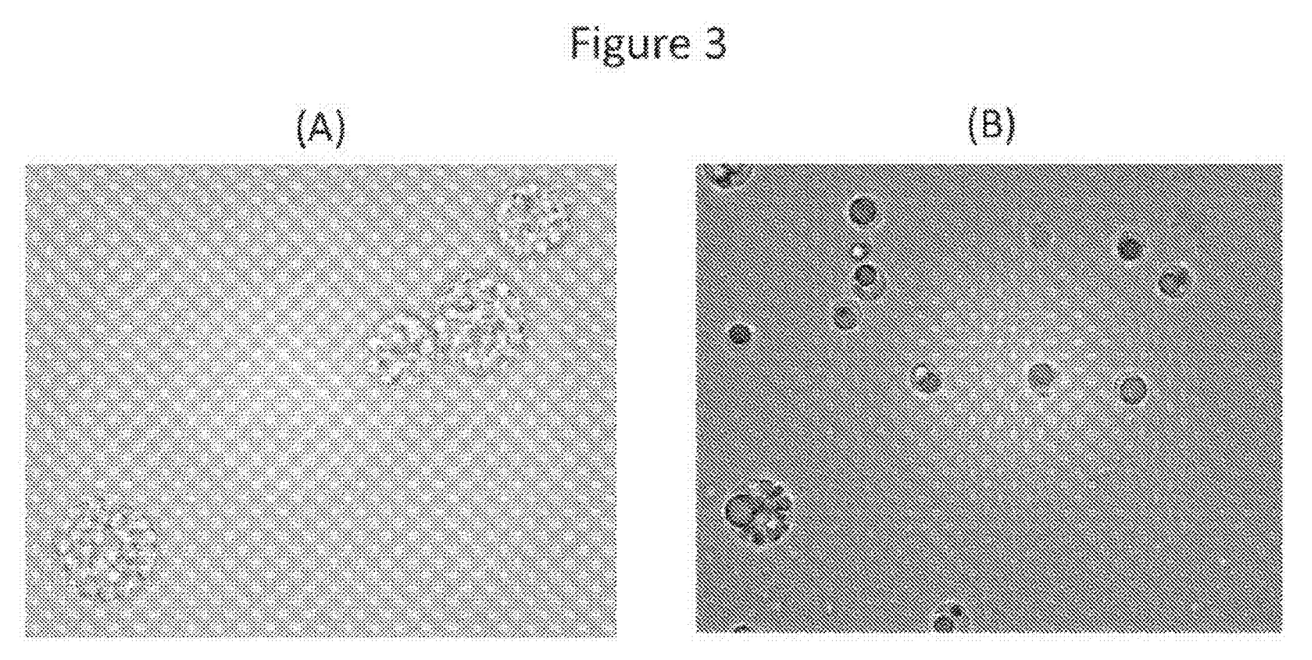
FIG. 3. Photonic microscopy images of cells having grown in medium containing $NH_4^+$ as nitrogen source. (A) Image of the strain FCC1324 (CCAP 4062-1). (B) Image of the strain FCC1104 of *Aurantiochytrium mangrovei* (CCAP4087/1). The two images have been taken with the same magnification ×1,000.

In addition the strains CCAP 4087/1 are smaller (see FIGS. 3A and 3B).

The invention relates to any strain of the Labyrinthulomycetes class, in particular of the genus *Aurantiochytrium*, capable of growing under mixotrophic culture conditions such as described in the present application, and capable of producing fatty acids such as DHA, and/or carotenoids such as astaxanthin, zeaxanthin, canthaxanthin, echinenone, beta-carotene and phoenicoxanthin.

The invention also relates to any species of protist of the genus *Aurantiochytrium*, capable of growing under mixotrophic culture conditions such as described in the present application, and capable of producing fatty acids such as DHA, and carotenoids such as canthaxanthin and/or astaxanthin.

The isolated strains of *Aurantiochytrium* according to the invention make it possible to produce, under mixotrophic conditions, significant quantities of biomass, as well as lipids and carotenoids, the lipids being rich in DHA. In fact, the method of the invention allows a biomass of *Aurantiochytrium* having 50% to 60% lipids with respect to the weight of the dry matter to be obtained. Said DHA may represent more than 15%, or more than 20%, or more than 30% of the total fatty acids contained in the protists, the carotenoids being rich in canthaxanthin and/or astaxanthin, and said canthaxanthin and/or astaxanthin may represent more than 0.01%, or more than 0.1%, or more than 0.2% by weight of the total weight of dry matter. The strains may attain a level of canthaxanthin and/or astaxanthin productivity (quantity of product of interest produced, per liter of culture, per hour) of 0.05 mg/L/h, or more than 1 mg/L/h, or more than 1.5 mg/L/h.

In the present invention, the strains of *Aurantiochytrium* (for example, the strains FCC 1324, FCC 31, FCC 1311, FCC 1319, FCC 1325 and FCC 1479, isolated by the applicant) that are cultured under mixotrophic conditions in the presence of variable and/or discontinuous illumination, in particular in the form of flashes, allow production of canthaxanthin and/or astaxanthin.

In contrast, under heterotrophic conditions, no canthaxanthin is detectable. Moreover, the quantities of biomass obtained in mixotrophic mode according to certain embodiments of the invention are equal to or even greater than (for example, by approximately 10 to 18%) the quantities obtained under heterotrophic conditions. By "heterotrophic conditions", it is meant culture conditions with an identical culture medium, but in the absence of light.

The invention thus relates to a method of culture of protist strains of the Labyrinthulomycetes class, notably of the Thraustochytrid families, in particular of the genus *Aurantiochytrium*, notably of the species *Aurantiochytrium* sp., in mixotrophic mode, in particular in the presence of an illumination that is variable or discontinuous over time, for example in the form of flashes, notably with a view to producing polyunsaturated fatty acids and carotenoids, such as DHA and canthaxanthin and/or astaxanthin.

The invention thus relates to a method for the production of DHA and/or of carotenoid(s), notably of canthaxanthin and/or astaxanthin by one or more strains of the genus *Aurantiochytrium*.

The invention thus relates to a method for selecting protist strains of the Labyrinthulomycetes class, notably of the Thraustochytrid and Labyrinthulid families, in particular, of the genus *Aurantiochytrium*, notably of the species *Aurantiochytrium* sp., with mixotrophic character, and having a high yield of polyunsaturated fatty acids and carotenoids, such as DHA and canthaxanthin and astaxanthin, in mixotrophic mode, in particular in the presence of an illumination that is variable and/or discontinuous over time.

According to an embodiment of the invention, the method for the production of DHA and/or of carotenoid(s), in particular of canthaxanthin and/or astaxanthin, comprises the culture in mixotrophic mode of one or more strains of the genus *Aurantiochytrium*.

According to an embodiment of the invention step a) can also comprise the following steps i and ii)

Step i) of growth under mixotrophic or heterotrophic conditions and

Step ii) of the accumulation of DHA and/or of carotenoids under mixotrophic conditions.

According to an embodiment of the invention, particularly suitable for the production of DHA and/or of carotenoid(s) on an industrial scale, step i) is carried out in continuous mode in a fermenter and step ii) comprises the continuous and successive feeding of n fermenters operating in semi-continuous mode, n being an integer equal to or greater than 2, with the cells produced in step i) and their culture under mixotrophic conditions.

Step i) is the growth phase of the cells making it possible to achieve a significant population. In general, a culture medium suitable for the culture of the strains of *Aurantiochytrium* is used.

Step ii) is a phase of accumulation of DHA and/or of carotenoid(s). Preferably, this phase uses a second feed solution making it possible to preferentially orient the metabolism towards the accumulation of these molecules of interest. For example, in case of production of DHA, this orientation can be done by increasing the ratio of the concentration of the carbon to that of the easily absorbed nitrogen (C/N ratio).

In practice, a first fermenter operating in continuous mode allows the growth (step i)) of the cells, and the outgoing flow (or draw-off) from this growth fermenter supplies the maturation tanks where the biomass is enriched with molecules of interest (step ii)).

According to this embodiment of the invention, the method can be described as a method called "uncoupled" as the growth phases according to step i) and maturation according to step ii) are physically and temporally separated.

Step i) of culture of the cells in continuous mode of the method for the production of biomass according to the invention, or "growth step", can be implemented in a fermenter known to one skilled in the art, such as for example, the "chemostat".

The start of the culture of step i) can be carried out in a standard fashion (see FIG. 1). Pre-culture steps can be carried out upstream, so as to obtain the desired cell concentration for starting the continuous production of biomass, namely between 2 and 50 g/L, preferably between 5 and 40 g/L.

In general, the increase in scale from the cryotube is carried out in several pre-culture steps. For example, it can be done in three steps, two steps in an Erlenmeyer (preculture 1 and preculture 2), and one step in a fermenter (pre-fermenter). The growth in the Erlenmeyer takes place in discontinuous ("batch") mode. In general, the growth in the pre-fermenter also takes place in discontinuous mode.

For example, the culture can pass progressively from a culture in the 20 mL Erlenmeyer to a culture in the 2 L Erlenmeyer, then to a culture in the fermenter (pre-fermenter) in discontinuous ("batch") mode, then, to a culture in a fermenter in continuous ("top fermenter") mode. For example, the fermenter in discontinuous mode has a volume of 40 L and the top fermenter has a volume of 4,000 L. The start of the culture in the top fermenter has an establishment phase during which the continuous regime is not attained, i.e. the growth of the cells is not stabilized, or is not in phase with the rate of feed with fresh medium. It is a phase of "attaining equilibrium" that could also be called "phase of attaining a steady state". This "phase of attaining a steady state" has a duration which depends on the growth rate of the microorganisms cultured or more precisely on the specific growth rate or $\mu max$. By way of example, this duration can be comprised between 5 and 200 hours, preferably between 10 and 100 hours.

Generally, once the steady state is attained, a draw-off rate from the top fermenter to the maturation fermenter(s) is established at a flow rate equivalent to the rate of feeding with fresh culture medium. This draw-off feeds a first maturation fermenter until the desired volume is transferred, then the draw-off is redirected to another maturation tank. One skilled in the art will know how to determine the volume of inoculum necessary according to the type of cells to be cultured, the molecule of interest to be produced and the capacities of the maturation tanks according to an embodiment. This volume of inoculum can be comprised between 10 and 90% of the capacity of the maturation fermenter, depending on the cells cultured; for example approximately 20%, 30%, 40%, 50%, 60%, 70%, or 80% of the capacity of the maturation fermenter.

The draw-off to the maturation fermenters is carried out in a standard fashion using known equipment.

Generally, a culture medium different from that used during step i) is employed during the maturation phase. According to the different embodiments, this culture medium is supplied in the maturation fermenter simultaneously to, or prior to, or subsequently to the inoculum originating from the draw-off from the top fermenter.

The volume of the culture in the fermenter of step i) is determined as a function of the final volume of culture desired for the cultures in the maturation fermenters. In general, the top fermenter has a volume of 5 to 100%, preferably 10% to 50% and more preferentially approximately 20% of the volume of the maturation fermenter that it feeds. For example, a top fermenter having a volume of 4,000 L can feed a maturation fermenter of 20,000 L. If the n maturation fermenters have different volumes, it is the volume of the largest fermenter which will determine the volume of the top fermenter.

Generally, the culture according to step i) of the strains of protists of the genus *Aurantiochytrium* for the production of DHA can be carried out in a saline culture medium (sea salt 10-20 g/L, preferably 15 g/L) with a glucose concentration from 5 to 200 g/L, preferably 30 to 100 g/L and more preferentially from 30 to 60 g/L. According to an embodiment, the culture medium also contains macronutrients, such as magnesium salts and potassium salts, at a concentration from 1 to 50 g/L, preferably 2 to 25 g/L. It also contains trace elements used in a standard fashion for the culture of protists, such as salts of manganese, zinc, cobalt, molybdenum and copper, nickel and iron. Typical values for the concentration of these trace elements are from 0.02 to 15 mg/L for each trace element. For example, the magnesium and zinc salts can be present at 2-4 mg/L, the cobalt and molybdenum salts can be present in a small quantity, such as 0.01-0.04 mg/L, preferably between 0.02 and 0.03 mg/L. The copper and nickel salts can be present at 1-4 mg/L, preferably at 1-2 mg/L. In general, the iron salts are present at a more significant level than the other salts, for example at a level of 8-15 mg/L.

According to an embodiment of the invention which is suitable for attaining very high cell densities (1 to $3 \times 10^9$ cells/nil), the culture medium called "Initial medium" in Table 1 below can be used for starting the continuous culture, and the feed solution of Table 1 is used to continuously supply the fermenters.

TABLE 1

Example of culture media useful for the culture of the strains of *Aurantiochytrium*, according to step i) of the culture method.

|  | Initial medium | Feed solution |
| --- | --- | --- |
| Carbon source | 1 to 1.6 CMol | 3.7 CMol |
| $NH_4^+$ | 1.5 to 7.5 g/L | 5 to 10 g/L |
| Sea salt | 5 to 30 g/L | 10 to 30 g/L |
| Ca | 25 to 70 mg/L | 100 to 200 mg/L |
| Mn | 1 to 10 mg/L | 4 to 20 mg/L |
| Zn | 0.1 to 1 mg/L | 0.5 to 2 mg/L |
| S | 0.5 to 1.5 g/L | 2 to 4 g/L |
| Co | 0.1 to 1 mg/L | 0.5 to 2 mg/L |
| Mo | 0.01 to 0.5 mg/L | 0.05 to 1.5 mg/L |
| Cu | 0.05 to 0.3 mg/L | 0.25 to 0.8 mg/L |
| Ni | 0.02 to 0.2 mg/L | 0.1 to 0.5 mg/L |
| K | 0.5 to 2 g/L | 3 to 5 g/L |
| Mg | 70 to 300 mg/L | 250 to 750 mg/L |
| P | 0.3 to 1 g/L | 1.3 to 2.5 g/L |
| Fe | 5 to 10 mg/L | 15 to 25 mg/L |
| Thiamine | 15 to 50 mg/L | 50 to 150 mg/L |
| Vitamin B12 | 0.2 to 0.7 mg/L | 0.7 to 2 mg/L |
| Panthotenate | 0.05 to 0.15 mg/L | 15 to 45 mg/L |
| Stabilizing agent (EDTA type) | To be decided by the laboratory assistant | To be decided by the laboratory assistant |

The "initial medium" corresponds to the medium which can be used for starting the continuous culture. Then "the feed solution" can be used for continuously supplying the fermenter.

According to the same embodiment, the nutritive solution used in the maturation step, step ii), contains a carbon source (for example glucose or glycerol), a nitrogen source (for example $(NH_4)_2SO_4$, a phosphate source (for example $KH_2PO_4$). Preferably, the ratio between the C (carbon), the N (nitrogen) and the P (phosphate) (C/N/P) is 530:11:1 always with the possibility of having up to times as much nitrogen (N) more or less, and/or up to twice as much phosphate (P) more or less, for example the following ratios can be used 530:22:1.530:5.5:1; 530:22:0.5; 530:11:2; 530: 22:2; 530:5.5:0.5; 530:11:0.5; 530:5.5:2.

The concentration ranges given for the medium used for the pre-culture, the discontinuous culture and the feed medium for the continuous culture are specifically adapted to the species Aurantiochytrium mangrovei, in particular the strain FCC 1324. Concentrations outside the recommended ranges can be used according to the species and the strain. By using the ranges described below as a basis one skilled in the art will be able to determine the composition adapted to the strain used, taking care to avoid deficiencies and inhibitions.

Generally, when the biomass concentration in the top fermenter has attained equilibrium, between approximately 5 and 100 g/L, preferably between approximately 10 and 70 g/L of biomass concentration, the draw-off from the top fermenter serves to continuously and successively feed the different maturation fermenters operating in semi-continuous mode. The culture of the cells is thus maintained under mixotrophic conditions in said fermenters ("maturation" step), with a view to the production of DHA and/or of carotenoid(s), in particular of canthaxanthin and/or astaxanthin. Thus, generally, feeding the maturation fermenters according to step ii) starts when the top fermenter is in a steady state with a stable cell density. Generally, for Aurantiochytrium this cell density could be between $10^7$ and $10^9$ cells per mL.

Feeding the maturation fermenters according to step ii) is (in general) carried out successively, i.e. a maturation fermenter n is fed with the draw-off from the top fermenter before passing onto the following maturation fermenter, n+1.

The volume of inoculum used for inoculating the maturation fermenter can represent between 10 and 70% of the final volume of the cell suspension in the maturation fermenter, preferentially between 20 and 60%, more preferentially between 30 and 50%.

Generally, once the desired volume of inoculum has been attained in the maturation fermenter n, the second (n+1) maturation fermenter (or "maturing vessel") is fed, then the third (n+2) maturation fermenter is fed, etc.

According to an embodiment, the culture in the maturation fermenter is stopped, then the fermenter is emptied when the production of DHA and/or of carotenoid(s) has attained the desired level, for example, when the DHA titre is between 5 and 30 g/L and/or the carotenoid titre between 0.1 and 10 mg/g of dry biomass.

Emptying is carried out in a standard fashion to devices allowing treatment of the biomass with a view to the extraction of the molecule(s) of interest. After having been emptied, the maturation fermenter is cleaned, generally with a specific piece of equipment which is incorporated into the tanks of the fermenters, then it is sterilized.

For example (see Table 2 and the diagram according to FIG. 1), with a culture time in the maturation fermenters of 72 h, on the first day, D, the maturation fermenter 1 is filled and the other maturation fermenters are waiting; on D+1, the maturation fermenter 2 is filled (culture N+2) and the maturation fermenter 1 is in the process of culturing; on D+2, the maturation fermenter 3 is filled and the maturation fermenters 1 and 2 are in the process of culturing; on D+3, the maturation fermenter 1 is cleaned, the maturation fermenter 4 is filled and the maturation fermenters 2 and 3 are in the process of culturing.

TABLE 2

|  | Maturation fermenter 1 | Maturation fermenter 2 | Maturation fermenter 3 | Maturation fermenter 4 |
|---|---|---|---|---|
| Day D | Culture N | Waiting | Waiting | Waiting |
| Day D + 1 | Culture N | Culture N + 1 | Waiting | Waiting |
| Day D + 2 | Culture N | Culture N + 1 | Culture N + 2 | Waiting |
| Day D + 3 | Cleaning and sterilization | Culture N + 1 | Culture N + 2 | Culture N + 3 |
| Day D + 4 | Culture N + 4 | Cleaning and sterilization | Culture N + 2 | Culture N + 3 |
| Day D + 5 | Culture N + 4 | Culture N + 5 | Cleaning and sterilization | Culture N + 3 |

The number of maturation fermenters fed by the top fermenter is greater than 2, and, generally, this number is limited only by the space available for storing said fermenters and their associated equipment. In general, the number of maturation fermenters is from 2 to 10, preferably from 2 to 6.

For the culture of Aurantiochytrium, the culture step in semi-continuous mode is generally carried out for 24 to 200 h in each fermenter, preferably for 48 h to 96 h, more preferentially 72 h to 96 h.

The composition of the culture medium for step ii) allows a residual growth to be maintained, while promoting the accumulation of DHA and/or of carotenoid(s), in particular of canthaxanthin and/or astaxanthin. By "residual growth", it is meant a multiplication of the cells at a growth rate comprised between 1 and 90% of the growth rate of step i) but which allows an improvement in productivity in terms of biomass and of the molecule(s) of interest.

For example, for the production of DHA by Aurantiochytrium FCC1324, the growth rate in continuous culture is from 0.05 to 0.20 $h^{-1}$, preferably 0.10 $h^{-1}$.

The growth rate characterizes the increase in the population over time. The growth rate ($\mu$) is calculated according to the formula:

$$\mu = (\ln N2 - \ln N1)/(t2 - t1)$$

where N1=quantity of biomass at time t1, N2: quantity of biomass at time t2. The quantity of biomass can be expressed in optical density, cell density or dry mass. The times t1 and t2 are expressed in hours. The value of $\mu$ is expressed in $h^{-1}$ (1/hour).

The culture medium used for the fermentation according to step ii) of semi-continuous culture is chosen in order to preferentially direct the metabolism of the cultured cells towards the accumulation of DHA and/or of carotenoid(s), in particular of canthaxanthin and/or astaxanthin. This is carried out during nitrogen limitation. By nitrogen limitation, it is meant a concentration of nitrogen in the culture medium insufficient to ensure the normal growth of the cells, which results in a modification of the metabolism promoting the accumulation of carbon in the form of lipids. This modification of the metabolism can also be obtained by increasing the C/N ratio (ratio of the concentration of carbon to that of easily absorbed nitrogen).

However, the culture medium contains an organic carbon-containing source, which allows mixotrophic or heterotrophic growth. Typically, for a protist culture, the organic carbon is present at a concentration from 10 to 90 g/l (from 55 mM to 500 mM).

In general, for the culture according to step ii) of maturation (for the production of DHA (and optionally of the carotenoids) by the strain Aurantiochytrium, the culture medium (reconstituted from the volume of the cell suspension originating from the top fermenter and from the volume of concentrated feed solution) comprises from 100 to 200 g/L of glucose, approximately 5 to 10 g/L of ammonium and 1 to 2 g/L of phosphate.

The culture method according to an embodiment of the invention is carried out under mixotrophic conditions and/or under heterotrophic conditions, i.e. step i) can be carried out independently under heterotrophic or mixotrophic conditions. Generally step ii) is carried out under mixotrophic conditions. According to an embodiment, step i) is carried out under heterotrophic conditions and step ii) under mixotrophic conditions. According to another embodiment, steps i) and ii) are carried out under mixotrophic conditions.

According to an embodiment, step ii) is carried out at a lower temperature than step i). The inventors have noted that, according to this embodiment, the quantity of lipids, in particular of DHA, produced is increased relative to a culture where step ii) is carried out at the same temperature as step i). In fact, according to the method of invention, the optimum temperature for growth is greater than the optimum temperature for the production of DHA. Generally, step ii) is carried out at 1 to 8 degrees less than the temperature at which step i) is carried out. For example, step i) of the culture can be carried out at 25° C., while step b) can be carried out at 18° C., 19° C., 20° C., 21° C., 22° C. or 23° C. For example, step i) of the culture can be carried out at 22° C., while step b) can be carried out at 18° C., 19° C., 20° C. or 21° C. For example, step i) of the culture can be carried out at 27° C., while step b) can be carried out at 20° C., 21° C., 22° C., 23° C., 24° C., 25° C. or 26° C. A low temperature also promotes the accumulation of pigments.

According to another aspect of the invention, the lighting conditions are adapted to maximize the yield of biomass, fatty acids, in particular of DHA and the carotenoids. It appeared that variable and/or discontinuous illumination of the cultures, in particular when used in a culture in mixotrophic mode, had a favourable impact on the development of the protists and made it possible to increase the productivity of the latter, notably as far as their lipids and carotenoids production is concerned. Without being bound to theory, the inventor believes that a discontinuous and/or variable light supply to the protists has the effect of causing a "stress" favourable to the growth and to the synthesis of lipids, as well as to the synthesis of carotenoids. This phenomenon may be partly explained by the fact that, in nature, protists tend to accumulate lipids and carotenoids reserves to withstand the constraints of their environment.

By "discontinuous illumination", it is meant an illumination punctuated by periods of darkness. The periods of darkness may be more than a quarter of the time, preferably half of the time or more, during which the algae are cultured.

According to a preferred aspect of the invention, the illumination is discontinuous and, more preferentially in the form of flashes. A flash, within the meaning of the invention, is an illumination with light of short duration, i.e. of less than 30 minutes. The duration may be less than 15 minutes, preferably less than 5 minutes or even more preferentially less than 1 minute. According to certain embodiments of the invention, the duration of the flash may be less than a second. For example, the duration of the flash may be $1/10$ of a second, or $2/10$ of a second, or $3/10$ of a second, or $4/10$ of a second, or $5/10$ of a second, or $6/10$ of a second, or $7/10$ of a second, or $8/10$ of a second, or $9/10$ of a second. The illumination with light, or the flash, generally lasts longer than 15 seconds. It is generally comprised between 5 seconds and 10 minutes, preferably between 10 seconds and 2 minutes, more preferentially between 20 seconds and 1 minute. These flash durations are suitable for light supplies of "low frequency".

According to this last embodiment, where the illumination regime (the light supply) is of "low frequency", the number of flashes is comprised between about 2 and 3,600 per hour. It may be, for example, comprised between 100 and 3,600 flashes per hour. It may also be comprised between 120 and 3,000, or between 400 and 2,500, or between 600 and 2,000, or between 800 and 1,500 flashes per hour. It may also be comprised between 2 and 200, preferentially between 10 and 150, more preferentially between 15 and 100, and even more preferentially between 20 and 50 per hour.

According to an embodiment, a flash has a duration between $1/150000$ second and $1/1000$ second. These flash durations are appropriate for "high frequency" illumination regimes; i.e. with flash frequencies from 150 kHz to 1 kHz respectively.

According to this embodiment where the illumination regime (the light supply) is of "high frequency", the flashes can occur between $3.6 \times 10^5$ and $5.4 \times 10^9$ times per hour. In this case the light variation is said to have a frequency of between 1 kHz and 150 kHz, i.e. between 1,000 and 150,000 flashes per second. The light supply according to this last embodiment of the invention is called "high frequency".

The number of flashes per hour is selected as a function of the intensity and duration of the flashes (see below). In general, the intensity of the light supplied in the form of flashes is between 5 and 1,000 $\mu mol \cdot m^{-2} \cdot s^{-1}$, preferably between 5 and 500 $\mu mol \cdot m^{-2} \cdot s^{-1}$, or 50 and 400 $\mu mol \cdot m^{-2} \cdot s^{-1}$, and more preferentially between 150 and 300 $\mu mol \cdot m^{-2} \cdot s^{-1}$. 1 $\mu mol \cdot m^{-2} \cdot s^{-1}$ corresponds to 1 $\mu E \ m^{-2} \cdot s^{-1}$ (Einstein), a unit often used in the literature.

According to another embodiment of the invention, the illumination may be variable, which means that the illumination is not interrupted by phases of darkness, but instead the light intensity varies over time. This variation of the light intensity is regular and may be periodic or cyclic. According to the invention, light may also be supplied combining phases of continuous and discontinuous illumination.

According to the invention, regardless of the illumination conditions, the light intensity supplied to the algae in culture, expressed in micromoles of photons per second per square meter ($\mu mol \cdot m^{-2} \cdot s^{-1}$), varies at least once in any one hour. The amplitude of this variation of light intensity is generally comprised between 5 and 1,000, or between 50 and 800, or between 100 and 600 $\mu mol \cdot m^{-2} \cdot s^{-1}$. The intensity of the light may also vary between 5 and 400 $\mu mol \cdot m^{-2} \cdot s^{-1}$. Preferably, the amplitude of the variation of light intensity is between 70 and 300 $\mu mol \cdot m^{-2} \cdot s^{-1}$ and more preferentially between 100 and 200 $\mu mol \cdot m^{-2} \cdot s^{-1}$.

Said light intensity may attain successively, under conditions of variable illumination, for example, the values 50 $\mu mol \cdot m^{-2} \cdot s^{-1}$ and 100 $\mu mol \cdot m^{-2} \cdot s^{-1}$, or 5 and 400 $\mu mol \cdot m^{-2} \cdot s^{-1}$, or 50 and 800 $\mu mol \cdot m^{-2} \cdot s^{-1}$ several times every hour. Said light intensity may attain successively, preferably, the values 50 and 200 $\mu mol \cdot m^{-2} \cdot s^{-1}$. Alternatively, under conditions of discontinuous illumination, said light intensity may attain successively, several times per hour, for example, the values 0 and 50 $\mu mol \cdot m^{-2} \cdot s^{-1}$, the values 0 and 100 $\mu mol \cdot m^{-2} \cdot s^{-1}$ or more preferentially the values 0 and 200 $\mu mol \cdot m^{-2} \cdot s^{-1}$. It may also attain successively, several times per hour, for example, the values 0 and 300 $\mu mol \cdot m^{-2} \cdot s^{-1}$, the values 0 and 600 $\mu mol \cdot m^{-2} \cdot s^{-1}$, the values 0 and 800 $\mu mol \cdot m^{-2} \cdot s^{-1}$ or again the values 0 and 1,000 $\mu mol \cdot m^{-2} \cdot s^{-1}$.

According to an embodiment of the invention, regardless of the illumination conditions, the intensity of the light supplied to the culture varies as a function of the cell density. The more dense the culture becomes, the more intense the light may be. The cell density is the number of cells per ml and it is measured by the techniques known to one skilled in the art.

At the initial stage of the culture, when the cell density is between about $10^6$ and $5 \times 10^6$ cells per ml, the light intensity may be between 5 and 15 $\mu mol \cdot m^{-2} \cdot s^{-1}$, preferably between 5 and 10 $\mu mol \cdot m^{-2} \cdot s^{-1}$. When the culture reaches a density between $10^7$ and $10^8$ cells per ml, the light intensity may be increased to between 15 and 200 $\mu mol \cdot m^{-2} \cdot s^{-1}$, for example, preferably between 20 and 50 $\mu mol \cdot m^{-2} \cdot s^{-1}$. When the culture, at the final stage, reaches a density between $10^8$ and $10^9$ cells per ml, the light intensity may be increased to between 50 and 700 $\mu mol \cdot m^{-2} \cdot s^{-1}$, for example, preferably between 50 and 150 $\mu mol \cdot m^{-2} \cdot s^{-1}$.

According to certain embodiments, for example, when the duration of the flashes is for example less than a minute, or less than a second, the intensity of the light may be higher than the values stated above. At the initial stage of the culture, when the cell density is between about $10^6$ and $5 \times 10^6$ cells per ml, the light intensity may be between 5 and 200 $\mu mol \cdot m^{-2} \cdot s^{-1}$, preferably between 5 and 100 $\mu mol \cdot m^{-2} \cdot s^{-1}$. When the culture reaches a density between $10^7$ and $10^8$ cells per ml, the light intensity may be increased to between 30 and 500 $\mu mol \cdot m^{-2} \cdot s^{-1}$, for example, preferably, between 50 and 400 $\mu mol \cdot m^{-2} \cdot s^{-1}$. When the culture, at the final stage, reaches a density between $10^8$ and $10^9$ cells per ml, the light intensity may be increased to between 100 and 1,000 $\mu mol \cdot m^{-2} \cdot s^{-1}$ for example, preferably, between 200 and 500 $\mu mol \cdot m^{-2} \cdot s^{-1}$.

According to an embodiment of the invention, the quantity of light supplied to the culture per hour remains between certain values. It is comprised between about 2,000 and 600,000, preferably between 2,000 and 300,000 $\mu mol \cdot m^{-2}$. It may be comprised between about 4,000 and 200,000 $\mu mol \cdot m^{-2}$ per hour.

According to an embodiment of the invention, the culture is illuminated with 30 flashes per hour, each flash having a duration of 30 seconds and an intensity of 10 $\mu mol \cdot m^{-2} \cdot s^{-1}$. The latter gives a total light supply per hour of 9,000 $\mu mol \cdot m^{-2}$. According to another embodiment of the invention, the culture is illuminated with 20 flashes per hour, each flash having a duration of 30 seconds and an intensity of 20 $\mu mol \cdot m^{-2} \cdot s^{-1}$. The latter gives a total light supply per hour of 12,000 $\mu mol \cdot m^{-2}$. According to another embodiment of the invention, the culture is illuminated with 45 flashes per hour, each flash having a duration of 15 seconds and an intensity of 5 $\mu mol \cdot m^{-2} \cdot s^{-1}$, which gives a total light supply per hour of 3,375 $\mu mol \cdot m^{-2}$.

According to another embodiment of the invention, the culture is illuminated with 120 flashes per hour, each flash having a duration of 10 seconds and an intensity of 200 $\mu mol \cdot m^{-2} \cdot s^{-1}$, which gives a total light supply per hour of 240,000 $\mu mol \cdot m^{-2}$.

According to another embodiment of the invention, the culture is illuminated with a frequency of 50 kHz, i.e. $1.8 \times 10^8$ flashes per hour, each flash having a duration of $1/100000$ seconds and an intensity of 200 $\mu mol \cdot m^{-2} \cdot s^{-1}$, which gives a total light supply per hour of 36,000 $\mu mol \cdot m^{-2}$.

As described for the light intensity above, and according to an embodiment of the invention, the quantity of light supplied to the culture per hour may vary as a function of the cell density. At the initial stage of the culture when the cell density is between $10^5$ and $5 \times 10^5$ cellsper ml, the total light supply per hour is generally comprised between about 1,500 and 8,000, preferably 1,500 and 6,000 $\mu mol \cdot m^{-2}$, more preferably between 2,000 and 5,000 $\mu mol \cdot m^{-2}$. When the culture reaches a density between $10^6$ and $10^7$ cells per ml, the total light supply per hour may be increased to between 6,000 and 67,000 $\mu mol \cdot m^{-2}$, preferably between 6,000 and 50,000 and more preferably between 12,000 and 45,000 $\mu mol \cdot m^{-2}$, for example. At the final stage of the culture, at a cell density between $10^7$ and $10^8$ cells per ml, the total light supply per hour may be increased to between 45,000 and 300,000, for example preferably between 45,000 and 200,000 $\mu mol \cdot m^{-2}$, and for example, yet more preferably, between 50,000 and 150,000 $\mu mol \cdot m^{-2}$.

According to an embodiment of the invention, in the initial stage of the culture (at a cell density between $10^5$ and $5 \times 10^5$ cells per ml), the culture is illuminated with 30 flashes per hour, each flash having a duration of 30 seconds and an intensity between 5 and 10 $\mu mol \cdot m^{-2} \cdot s^{-1}$, which gives a total light supply per hour from 2,250 $\mu mol \cdot m^{-2}$ to 4,500 $\mu mol \cdot m^{-2}$. Then, at the intermediate stage (at a cell density between $10^6$ and $10^7$ cells per ml), the culture is illuminated with 30 flashes per hour, each flash having a duration of 30 seconds and an intensity between 15 and 50 $\mu mol \cdot m^{-2} \cdot s^{-1}$, which gives a total light supply per hour of 13,500 to 45,000 $\mu mol \cdot m^{-2}$. Then, at the final stage of the culture (at a cell density between $10^7$ and $10^8$ cells per ml), the culture is illuminated with 30 flashes per hour, each flash having a duration of 30 seconds and an intensity between 50 and 150 $\mu mol \cdot m^{-2} \cdot s^{-1}$, which gives a total light supply per hour of 45,000 to 135,000 $\mu mol \cdot m^{-2}$.

According to an embodiment of the invention, for example when the duration of the flashes is for example less than a minute, or less than a second, in the initial stage of culture (at a cell density between $10^5$ and $5 \times 10^5$ cells per ml), the culture is illuminated with 30 flashes per hour, each flash having a duration of 10 seconds and an intensity between 50 and 100 $\mu mol \cdot m^{-2} \cdot s^{-1}$, which gives a total light supply per hour from 15,000 $\mu mol \cdot m^{-2}$ to 30,000 $\mu mol \cdot m^{-2}$. Then at the intermediate stage (at a cell density between $10^6$ and $10^7$ cells per ml), the culture is illuminated with 50 flashes per hour, each flash having a duration of 10 seconds and an intensity between 200 and 300 $\mu mol \cdot m^{-2} \cdot s^{-1}$, which gives a total light supply per hour of 100,000 to 150,000 $\mu mol \cdot m^{-2}$. Then, at the final stage of the culture (at a cell density between $10^7$ and $10^8$ cells per ml), the culture is illuminated with 120 flashes per hour, each flash having a duration of 10 seconds and an intensity between 350 and 450 $\mu mol \cdot m^{-2} \cdot s^{-1}$, which gives a total light supply per hour of 420,000 to 540,000 $\mu mol \cdot m^{-2}$.

The light supply to the cultures may be obtained by light sources distributed around the external wall of the fermenters. A clock triggers these lamps for defined illumination times. According to a preferred embodiment, the lighting of the cultures is ensured by an illumination device internal to the fermenter. Thus, the effectiveness of the illumination is better relative to a configuration where the light penetrates via windows from sources arranged on the outside. The illumination devices can be arranged on the revolving assembly equipped with blades or on the tubular parts immersed in the mass to be treated, or also at the bottom or the top of the tank. According to a preferred embodiment of the invention, the illumination device is situated on the baffles inside the fermenter. Such a device is described in the French patent application No. 1353641. The fermenter is thus equipped with a plurality of illumination sources borne by baffles, the latter having the function of preventing the formation of a vortex within the biomass under the action of the revolving mixing assembly. These illumination sources are preferably encapsulated, partially or completely in at least one part of these baffles, in a material that is compatible with the biomass and of a thickness that makes it possible to diffuse said light inside the tank.

A particularly suitable material is polysulphone which combines a good compatibility with food standards (including the American standards of the Food and Drug Administration, or abbreviated to FDA), a good heat transfer coefficient (allowing removal of the heat to the mass of micro-organisms and a semi-transparent character allowing good transmission of light, if the material has a thickness chosen between 1 mm and 5 cm; moreover, this material retains its properties after an optional heat treatment for sterilization or for cleaning with detergents or acid. If the combination of desired characteristics is modified, other materials can be chosen, for example polyurethane, polypropylene, an acrylic material or a polycarbonate.

Preferably, the illumination sources are light emitting diodes (abbreviated to LED); they are light sources that are easy to control, both in their implementation and in their applications. Such sources can have very diverse emission spectra, as there are white LEDs (simulating sunlight), but also LEDs with a reduced spectral range (for example centred on red, blue or green light). Such illumination sources generate less heat than bulbs or lamps; moreover they have dimensions which are sufficiently small to be able to be located on the faces of the baffles without leading to an increased thickness which interferes with the main function of these plates.

The spectrum of the illumination sources is advantageously in the visible range, but can also, depending on requirements, be outside this visible range, for example in the UV (for example for applications involving sterilization), or in the infra-red (for example, in applications aimed at generating heat within the mass to be treated).

The illumination sources can have very varied control regimes (also termed monitoring or management regimes).

As the applicant could ascertain, the fact that the thus cultured strains have good growth capabilities in mixotrophic mode, in the presence of discontinuous and/or variable light, predisposes said strains to a higher production of polyunsaturated fatty acids and carotenoids, notably DHA and canthaxanthin and/or astaxanthin.

The culture method according to the invention allows lipids and carotenoids to be produced.

In this case, the method according to certain embodiments of the invention also comprises the following steps:

a) culture, in mixotrophic mode, of one or more strains of the Labyrinthulomycetes class, in particular, of the genus *Aurantiochytrium* under mixotrophic conditions, in particular in the presence of an illumination that is discontinuous and/or variable over time, the illumination having variations in intensity, the amplitude of which is comprised between 5 $\mu mol \cdot m^{-2} \cdot s^{-1}$ and 1,000, preferably between 5 and 400 $\mu mol \cdot m^{-2} \cdot s^{-1}$, these variations taking place between 2 and 3,600, preferably 5-400 times per hour, b) a step of maintaining said culture over several generations, in the presence of an organic carbon-containing substrate in the culture medium, and optionally c) a step of recovery of the thus cultured protists.

By "step of recovery", it is meant more particularly the isolation of the strain or strains for which the number of cells increased the most during said generations.

d) a step of recovery of the hydrophobic matter of the protists, and optionally e) the extraction of DHA (docosahexaenoic acid) and carotenoids, in particular of canthaxanthin and/or astaxanthin from the recovered hydrophobic matter.

The hydrophobic matter in fact comprises the lipids and the carotenoids.

The method of culture according to the invention may also be applied to any species of the genus *Aurantiochytrium*, capable of growing under the mixotrophic conditions according to the invention, and capable of producing DHA and carotenoids.

Therefore, the invention is also directed to optimizing the production of biomass, as well as the production of lipids and carotenoids, notably of DHA, and/or canthaxanthin and/or astaxanthin through the culture of protists of the genus *Aurantiochytrium* with mixotrophic character, preferably cultured or selected according to the methods mentioned above, then the recovery of the thus cultured protists in order to extract the hydrophobic content therefrom, in particular the lipids including DHA, and the carotenoids, including canthaxanthin and astaxanthin.

According to embodiments of the method for the production of DHA and/or of canthaxanthin and/or astaxanthin, described previously, the quantities of biomass obtained are greater than 100 g/L, preferably greater than 110 g/L or more preferentially greater than 140 g/L. The lipids are present in this biomass at a level greater than 40%, or even 50%. In general the DHA represents more than 15%, or even 20%, or even 30%, or even more than 35% of the fatty acids. Canthaxanthin and/or astaxanthin can represent between 0.01%, and 0.2% by weight relative to the total weight of dry matter.

The methods for selectively extracting the lipids, including DHA, are known to one skilled in the art and are, for example, described by [Bligh, E. G. and Dyer, W. D. (1959); A rapid method of total lipid extraction and purification, Can. J. Biochem. Physiol., 37: 911-917].

The methods of extraction and analysis of the carotenoids, including lutein, are known to one skilled in the art and are, for example, described by Wright et al. (1991) (S. W. Wright, S. W. Jeffrey, R. F. C. Mantoura, C. A. Llewellyn, T. Bjornland, D. Repeta, N. Welschmeyer: Improved HPLC method for the analysis of chlorophylls and carotenoids from marine phytoplankton. Marine Ecology Progress Series: Vol. 77: 183-196, 1991).

The invention also relates to the protists of the Labyrinthulomycetes class, notably of the Labyrinthulaceae and Thraustochytriaceae families, in particular of the genus *Aurantiochytrium*, which can be obtained according to the method of the invention as described above. These protists are enriched with polyunsaturated fatty acids and carotenoids. The total lipids of such protists generally comprise more than 40%, or more than 50%, or more than 60% by weight of the dry matter. Generally, they can have a DHA titre of 10 g/L to 20 g/L. The canthaxanthin and/or astaxanthin contained in such protists, according to an embodiment of the invention, may represent more than 0.1%, or more than 0.15%, or more than 0.2% by weight of the total weight of dry matter. The protists according to an embodiment of the invention may thus have a productivity (quantity of product of interest produced, per liter of culture, per hour) of canthaxanthin and/or astaxanthin of 0.05 mg/L/h, or more than 1 mg/L/h, or more than 1.5 mg/L/h. They can also have a productivity of DHA of at least 0.1 g/L/h, preferably 0.2 g/L/h DHA, and more preferentially of at least 0.3 g/L/h DHA.

Example 1

The cultures of *Aurantiochytrium* are carried out in 1 to 2 L capacity fermenters (bioreactors) for use with dedicated automatic controllers and computerized supervision. The pH of the system is adjusted by adding base (a 2N sodium hydroxide solution) and/or acid (a 1N sulphuric acid solution). The culture temperature is set to 26° C. Stirring is carried out using 3 stirring rotors mounted on the shaft according to the Rushton configuration (three-blade impellers with downward pumping). The dissolved oxygen pressure is regulated in the medium throughout culture, by the stirring speed (250-600 rpm), the air flow rate (0.25-1 vvm), or the oxygen flow rate (0.1-0.5 vvm). The control parameters, integrated into the automatic supervision system, make it possible to maintain a constant $pO_2$ at 15%. The bioreactor is equipped with an external lighting system surrounding the transparent tank. The intensity as well as the light cycles are controlled by a dedicated automatic device, under computerized supervision.

The reactors are inoculated with a preculture prepared on a mixing table (140 rpm) in a temperature-controlled chamber (26° C.) and illuminated between 100 and 200 μE. Pre-cultures and cultures in the bioreactors are carried out in the modified Verduyn medium (sea salts 15 g/L, $(NH_4)_2SO_4$ 3 g/L, $KH_2PO_4$ 1 g/L, $MgSO_4.7H_2O$ 0.5 g/L, $Na_2EDTA$ 24 mg/L, $ZnSO_4.7H_2O$ 3 mg/L, $MnCl_2.2H_2O$ 3 mg/L, $Na_2MoO_4.2H_2O$ 0.04 mg/L, $FeSO_4.7H_2O$ 10 mg/L, pantothenate 3.2 mg/L, thiamine hydrochloride 9.5 mg/L, vitamin B12 0.15 mg/L). The carbon-containing substrate used for the culture under conventional mixotrophic conditions, under heterotrophic conditions and under mixotrophic conditions with flash (variable/discontinuous light) in the bioreactor is glucose at concentrations between 300 mM and 1 M.

Monitoring of the Cultures:

The concentration of total biomass is monitored by measuring the dry mass (filtration on a Whatman GF/F filter, then oven drying, at 105° C., for min. 24 h before weighing).

Regarding the quantification of the total lipids, $10^8$ cells/mL were extracted. Methods for extracting lipids are known to one skilled in the art.

For the quantification of the carotenoids and notably canthaxanthin and astaxanthin, $10^8$ cells/mL were extracted. Methods for extraction and analysis of the carotenoids, including canthaxanthin and astaxanthin, are known to one skilled in the art.

Illumination (for Culture Under Mixotrophic Conditions):

The culture is illuminated with 30 flashes per hour, each flash having a duration of 30 seconds and an intensity of 200 $\mu mol \cdot m^{-2} \cdot s^{-1}$.

The supply of light to the cultures in the bioreactor was obtained by LED lamps distributed around the external wall of the fermenter. A clock triggers these LED lamps for illumination times or pulses (for culture under flash mixotrophic conditions with discontinuous light).

TABLE 3

Results of Example 1 (n = 3):

| | Dry mass (g/L) | Total lipids (% of dry mass) | % DHA (total fatty acids) | Astaxanthin (mg/g of dry mass) |
|---|---|---|---|---|
| Mixotrophy with flashes | 115 +/− 2 | 56 +/− 3.6 | 18.3 +/− 2.8 | 1.1 +/− 0.1 |
| Heterotrophy | 112.2 +/− 1.6 | 44.5 +/− 2.9 | 19.1 +/− 2.5 | 0 |

Example 2

The production of an oil rich in DHA and in canthaxanthin by the strain FCC 1324 of the genus *Aurantiochytrium* is described below.

Step i):

The cultures of *Aurantiochytrium* are carried out in 1 to 2 L fermenters (bioreactors) for use with dedicated automatic controllers and computerized supervision. The pH of the system is adjusted by adding base (a 2N sodium hydroxide solution) and/or acid (a 1N sulphuric acid solution). The culture temperature is set to 26° C. Stirring is carried out using 3 stirring rotors mounted on the shaft according to the Rushton configuration (three-blade impellers with downward pumping). The dissolved oxygen pressure is regulated in the medium throughout culture, by the stirring speed (250-600 rpm), the air flow rate (0.25-1 vvm), or the oxygen flow rate (0.1-0.5 vvm). The control parameters, integrated into the automatic supervision system, make it possible to maintain a constant $pO_2$ at 15%. The bioreactor is equipped with an internal light system fixed on the baffles. The intensity, as well as the light cycles, are controlled by a dedicated automatic device, under computerized supervision. The culture is illuminated with 60 flashes per hour, each flash having a duration of 20 seconds and an intensity of 100 $\mu mol \cdot m^{-2} \cdot s^{-1}$.

The reactors are inoculated with a preculture prepared on a mixing table (140 rpm) in a temperature-controlled chamber (26° C.) and illuminated between 100 and 200 μE. Pre-cultures and cultures in the bioreactors are carried out in the modified Verduyn medium (sea salts 15 g/L, $(NH_4)_2SO_4$ 3 g/L, $KH_2PO_4$ 1 g/L, $MgSO_4.7H_2O$ 0.5 g/L, $Na_2EDTA$ 24 mg/L, $ZnSO_4.7H_2O$ 3 mg/L, $MnCl_2.2H_2O$ 3 mg/L, $Na_2MoO_4.2H_2O$ 0.04 mg/L, $FeSO_4.7H_2O$ 10 mg/L, pantothenate 3.2 mg/L, thiamine hydrochloride 9.5 mg/L, vitamin B12 0.15 mg/L). The carbon-containing substrate used is glucose at concentrations between 60 and 200 g/L.

Continuous feeding with fresh medium is carried out with a dilution level of approximately 0.08 to 0.15 $h^{-1}$ and with a medium concentrated between 10 and 15 times the initial concentration of each element. One skilled in the art will be able to determine how to implement the continuous culture and calculate the feed flow rate, as well as to determine when the steady state is attained.

Once the steady state is attained, the continuous draw-off from this fermenter can serve to feed the maturation fermenter of step b).

Step ii):

The cultures of *Aurantiochytrium* are carried out in 10 to 20 L fermenters (bioreactors) used with dedicated automatic controllers and supervision by computerized supervision. The regulation systems as well as the parameterization of the latter are, in every respect, similar to those of step i).

The reactors are inoculated with approximately 50% of the total culture volume of the draw-off from step i); and at the same time, the tank is also fed at the same flow rate with a medium concentrated twice, which makes it possible to obtain the following final composition: sea salts 15 g/L, glucose between 60 and 120 g/L, $(NH_4)_2SO_4$ at 0.8 gL; $KH_2PO_4$ 1 g/L, $MgSO_4.7H_2O$, 0.5 g/L, $Na_2EDTA$ 24 mg/L, $ZnSO_4.7H_2O$ 3 mg/L, $MnCl_2.2H_2O$ 3 mg/L, $Na_2MoO_4.2H_2O$ 0.04 mg/L, FeSO4.7$H_2O$ 10 mg/L, pantothenate 3.2 mg/L, thiamine hydrochloride of 9.5 mg/L, vitamin B12 0.15 mg/L.

The culture is illuminated with 60 flashes per hour, each flash having a duration of 20 seconds and an intensity of 500 μmol.

Monitoring of the Cultures:

The concentration of total biomass is monitored by measuring the dry mass (filtration on a Whatman GF/F filter, then oven drying, at 105° C., for min. 24 h before weighing).

Regarding the quantification of the total lipids, about $10^8$ cells were extracted. Methods for extracting lipids are known to one skilled in the art.

For the quantification of the carotenoids and notably canthaxanthin, $10^8$ cells were extracted. Methods for extraction and analysis of the carotenoids, including canthaxanthin, are known to one skilled in the art.

TABLE 4

Results of Example 2 (n = 3)

| Dry mass (g/L) | Total lipids (% of the DM) | % DHA | Canthaxanthin (mg/g of DM) |
|---|---|---|---|
| 155 +/− 3.3 | 55 +/− 2.8 | 18.0 +/− 3.0 | 2.1 +/− 0.3 |

Example 3

The continuous production of a biomass with a high cell density low in fatty matter (5 to 10%) then the accumulation of fatty acids by maturation of this biomass.

Step i): Continuous Culture for the Production of Biomass

The cultures of *Aurantiochytrium* are carried out in 1 to 2 L reactors for use with dedicated automatic controllers and computerized supervision. The pH of the system is adjusted by adding base (a 2N sodium hydroxide solution) and/or acid (a 1N sulphuric acid solution). The culture temperature is set to 26° C. Stirring is carried out using 3 stirring rotors: 1 Rushton turbine with 6 straight blades positioned at the lower end of the stirring shaft above the sparger and 2 three-blade propellers placed on the stirring shaft (distance between the stirring rotors=1.5× the diameter of a propeller).

The dissolved oxygen pressure is regulated in the medium throughout the culture, by the speed of rotation of the stirring shaft (250-600 rpm), ventilation with air (0.25-1 vvm) or with oxygen (0.1-0.5 vvm). The regulation parameters, incorporated in the automatic supervision controller, make it possible to maintain a constant pO2 at 15%.

The fermenter is equipped with an internal light system fixed to the baffles.

The intensity and the frequency of the illumination cycles are controlled by a dedicated automatic controller with computerized supervision. The culture is illuminated with 60 flashes per hour, each flash having a duration of 20 seconds and an intensity of 100 µmol·m−2·s−1.

The pre-culture is carried out on a mixing table (140 rpm) in a temperature-controlled chamber (26° C.) and illuminated between 100 and 200 µE. The reactor is inoculated at 1% from the pre-culture and operated in discontinuous mode.

Once the substrate contained in the initial medium is consumed and the desired cell density is attained, the draw-off of the culture medium, on the one hand, and the supply of feed solution, on the other hand, are started. The steady state is attained after at least 5 residence times. Once the steady state has stabilized, the operating parameters (ventilation flow rate, power consumption, feed flow rate, pH, volume of mash), the residual concentration of substrate in the mash, as well as the macromolecular concentration and composition of the biomass produced are constant.

For the strain FCC 1324, the composition of the feed solution chosen and the dilution level selected make it possible to produce a volume of mash equivalent to 2.4 times the volume of the fermenter each day.

The regime is considered stable at the end of 50 hours of culture. Once the regime has stabilized, the residual glucose concentration in the mash stabilizes around 0 g/L, the cell density stabilizes around $3 \times 10^9$ cells/mL, which corresponds to approximately 65 g/L of biomass, the content of fatty matter in the biomass stabilizes around 5% (g Fatty Matter/g Dry Matter). The fermentation in continuous mode has been maintained for a total duration of 890 hours, 815 hours of which are under stabilized conditions.

For this example the level of dilution with the feed solution is set at half of the maximum growth rate of the strain on the medium used and under the culture conditions used.

The draw-off flow rate of the medium is adapted in order to take account of the flow rate of the feed solution but also the volume of liquid for correcting the pH.

The composition of the culture medium for starting the culture in batch mode is detailed in Table 1.

The feed solution of the continuous culture contains 15 g/L of commercial sea salt (e.g. INSTANT OCEAN salts), 110 g/L of glucose, and contains concentrations of trace elements, macronutrients and vitamins equivalent to approximately 3 times those contained in the medium used for the pre-culture and the discontinuous culture. Other compositions for the feed solution are possible, as detailed in Table 1.

The concentration of total biomass is monitored by measurement of the dry mass (filtration on GF/F, Whatman, filter then oven drying at 105° C., for a minimum of 24 h before weighing).

Regarding the quantification of the total lipids, approximately $10 \times^8$ cells were extracted. The methods for extraction of the lipids are known to one skilled in the art.

For the quantification of the carotenoids, and in particular canthaxanthin, $10 \times^8$ cells were extracted. Methods for extraction and analysis of the carotenoids, including canthaxanthin, are known to one skilled in the art.

TABLE 5

Characteristics of the steady state obtained in continuous culture.

| Residual glucose | 0.1 ± 0.02 | g/L |
|---|---|---|
| Cell density | 3.109 +/− 0.5.109 | cells/mL |
| Dry Mass | 65 +/− 5 | g/L |
| Fatty acid content | 7% +/− 3% | % |

Step ii) Maturation

The mash produced in continuous culture therefore has a high cell density of a biomass with a very low lipid content (5 to 10%). This biomass is transferred into a maturation tank under culture conditions where it very rapidly accumulates fatty acids (65 G/L in 24 hours). This allows a high concentration of biomass rich in fatty acid to be produced.

In this example, several maturation tests are carried out starting from the mash originating from the fermenter operated in chemostat mode. The cultures are carried out in 3 to 5 L fermenters (bioreactors) for use with dedicated automatic controllers and computerized supervision. The regulation systems as well as the settings of the latter are, in every respect, similar to those in step 1.

In the case of the maturation tests described in this example, the volume taken from the continuous culture is taken in one go. In the case of an industrial fermentation, this transfer is carried out progressively by drawing-off the culture medium.

In the maturation tank, the nutritive solution with a C/N/P ratio of 530:11:1 is progressively added to the volume taken.

The nutritive solution is added into the maturation tank each time that the carbon source (in this case glucose) is exhausted.

The monitoring of the discontinuous culture supplied, carried out in the maturation tank, is carried out according to protocol which is in every respect identical to that of step i). The results are given in Table 5.

TABLE 6

Dry matter, fatty acids and DHA produced in 24 hours and in 48 hours during maturation at 25° C. and at a pH of 6.5 (5 repetitions)

|  | 24 Hours of culture | 48 Hours of culture |
| --- | --- | --- |
| Dry matter | 160 g/L (+/− 2 g/l) | 185 g/l (+/−5 g/l) |
| Fatty acids | 67 g/L (+/−2 g/l) | 85 g/l (+/−5 g/l) |
| DHA | 16.5 g/L(+/−0.5 g/l) | 21 g/L (+/−2 g/l) |
| Astaxanthin | 0.05 mg/g MS (+/−0.01) | 0.07 mg/g MS (+/−0.01) |

The invention claimed is:

1. Method for the production of docosahexaenoic acid (DHA) and/or of one or more carotenoids comprising the following steps:
   a) culture in mixotrophic mode a strain of the genus *Aurantiochytrium* in a culture medium comprising an organic carbon-containing substrate selected from the group consisting of saccharose, glycerol at a concentration from 100 mM to 1.5 M, glucose and mixtures thereof to produce a biomass of the strain of the genus *Aurantiochytrium* comprising DHA and/or one or more carotenoids wherein the culture consists of the following two steps:
      Step i) of growth under mixotrophic or heterotrophic conditions at a temperature from 22° C. to 27° C., and
      Step ii) of accumulation of DHA and/or of carotenoids under mixotrophic conditions at a temperature from 19° C. to 25° C., and
      wherein step ii) is carried out at a temperature 1 to 3 degrees lower than step i),
   b) recovery of the biomass of the strain of the genus *Aurantiochytrium* comprising DHA and/or one or more carotenoids produced in step a), and
   c) extraction of DHA and/or one or more carotenoids from the recovered biomass of step b)
   wherein the strain of the genus *Aurantiochytrium* is the strain FCC 1324, deposited at the CCAP (Culture Collection of Algae and Protozoa), under the accession number CCAP 4062/1, and
   wherein the culture in mixotrophic mode is carried out under illumination conditions that are discontinuous in the form of flashes having a duration comprised between 1/10 second and 10 minutes, the illumination having variations in intensity the amplitude of which is comprised between 70 µmol·m$^{-2}$s$^{-1}$ and 300 µmol·m$^{-2}$s$^{-1}$, these variations in intensity taking place between 2 and 3,600 times per hour.

2. Method according to claim 1, wherein step is carried out in continuous mode in a fermenter and step ii) comprises the continuous and successive feeding of n fermenters operating in semi-continuous mode, n being an integer equal to or greater than 2, with the cells produced in step i) and their culture under mixotrophic conditions.

3. Method according to claim 1, wherein the number of flashes is between $3.6 \times 10^5$ and $5.4 \times 10^9$ per hour.

4. Method according to claim 1, wherein the number of flashes is between 5 and 3,600 per hour.

5. Method according to claim 1, wherein the one or more carotenoids is selected from the group consisting of canthaxanthin, astaxanthin and mixtures thereof.

6. Method according to claim 1, wherein step i) of growth under mixotrophic or heterotrophic conditions is at a temperature of 26° C., and Step ii) of accumulation of DHA and/or of one or more carotenoids under mixotrophic conditions is at a temperature of 25° C.

* * * * *